United States Patent [19]
Randall et al.

[11] Patent Number: 5,116,821
[45] Date of Patent: May 26, 1992

[54] SULFATED GLYCEROGLUCOLIPIDS AS INHIBITORS OF BACTERIAL ADHERENCE

[75] Inventors: Jared L. Randall, North Bend; Robert D. Leunk, Cincinnati, both of Ohio

[73] Assignee: The Proctor & Gamble Company, Cincinnati, Ohio

[21] Appl. No.: 616,285

[22] Filed: Nov. 20, 1990

[51] Int. Cl.$^5$ .............................. A01N 43/04
[52] U.S. Cl. ...................... 514/25; 514/53; 514/54; 514/61
[58] Field of Search ............... 514/25, 54, 61, 53

[56] References Cited

U.S. PATENT DOCUMENTS 4,464,360  8/1984  Leffler ............................ 424/180
4,912,093  3/1990  Michaeli ............................ 514/53

OTHER PUBLICATIONS

Slomiany et al "Sufation of Glycolipids." Digestion 36:246–252 (1987).

Gigg, R., "The Allyl Ether as a Protecting Group in Carbohydrate Chemistry Part 10. Synthesis of 3-0-(-β-D-Galactopyranosyl 3-sylphate)-2-O-hexadecanoyl-1-O-hexadecyl-L-glycerol, 'Seminolipid'", Journal of the Chemical Society, Perkin Transactions 1, No. 3 (1979), pp. 712–718.

Gigg, R., "Studies on the Synthesis of Sulfur-Containing Glycolipids (Sulfoglycolipids)", Carbohydrate Sulfates, American Chemical Society Symposium Series, vol. 77 (1978), pp. 44–66.

Slomiany, B. L., J. Piotrowski, A. Samanta, K. VanHorn, V. L. N. Murty & A. Slomiany, "Campylobacter pyrlori Colonization Factor Shows Specificity for Lactosylceramide Sulfte and GM3 Ganglioside", Biochemistry International, vol. 19, No. 4, (Oct. 1989), pp. 929–936.

Lingwood, C. A., H. Law, A. Pellizzari, P. Sherman & B. Drumm, "Gastric Glycerolipid as a Receptor for Camplobacter pylori", The Lancett, Jul. 29, 1989, pp. 238–241.

Primary Examiner—Frederick E. Waddell
Assistant Examiner—Gregory Hook
Attorney, Agent, or Firm—Milton B. Graff, IV.; Jerry J. Yetter; Richard C. Witte

[57] ABSTRACT

The subject invention involves pharmaceutical compositions comprising a sulfated glyceroglucolipid having the structure:

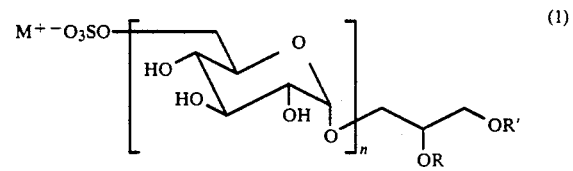

wherein n is an integer of from 1 to about 5, R is hydrogen or $C_1$–$C_{24}$ acyl or alkyl, R' is hydrogen or $C_1$–$C_{24}$ acyl or alkyl, and $M^+$ is a cationic moiety, and methods of treating or preventing gastroduodenal diseases or disorders caused by or associated with H. pylori by administering such compounds.

19 Claims, No Drawings

SULFATED GLYCEROGLUCOLIPIDS AS INHIBITORS OF BACTERIAL ADHERENCE

TECHNICAL FIELD

The subject invention relates to compounds which inhibit the adherence of *Helicobacter pylori* to mucosal surfaces, such that the compounds are useful in the prevention or treatment of gastrointestinal disorders and diseases caused or mediated by *H. pylori*.

BACKGROUND OF THE INVENTION

*Helicobacter pylori* is an important human pathogen which causes chronic, active inflammation of the stomach (gastritis), and is probably a major predisposing cause of gastric and duodenal ulcers (peptic ulcer disease). This bacterium was first cultured and identified in 1982. Previously called *Campylobacter pyloridis* and *Campylobacter pylori*, the bacterium was placed in a new genus and named *Helicobacter pylori* in 1989; see Goodwin, C. S., J. A. Armstrong, T. Chilvers, M. Peters, M. D. Collins, L. Sly, W. McConnell & W. E. S. Harper, "Transfer of *Campylobacter pylori* and *Campylobacter mustelae* to Helicobacter gen. nov. as *Helicobacter pylori* comb. nov. and Helicobacter mustelae comb. nov., Respectively", *International Journal of Systematic Bacteriology*, Vol. 39, No. 4 (Oct. 1989), pp. 397–405. References which disclose adherence characteristics of *H. pylori* to certain cells include Evans, D. G., D. J. Evans, Jr., J. J. Moulds & D. Y. Graham, "N-Acetyl-neuraminyllactose-Binding Fibrillar Hemagglutinin of *Campylobacter pylori*: a Putative Colonization Factor Antigen", *Infection and Immunity*. Vol. 56, No. 11 (Nov. 1988), pp. 2896–2906; and Evans, D. G., D. J. Evans, Jr. & D. Y. Graham, "Receptor-Mediated Adherence of *Campylobacter pylori* to Mouse Y-1 Adrenal Cell Monolayers", *Infection and Immunity*, Vol 57, No. 8 (Aug. 1989), pp. 2272–2278.

A general review of sulfated glyceroglucolipids and related compounds is found in Slomiany, B. L. & A. Slomiany, "Lipids of Mucous Secretions of the Alimentary Tract", *Attachment of Organisms to the Gut Mucosa*, Boedeker, ed., Vol. II (1984), CRC Press, pp. 24–31. Certain sulfated glyceroglucolipids have been isolated from a lipid extract of human gastric content as reported in Slomiany, B. L., A. Slomiany & G. B. J. Glass, "Glycolipids of the Human Gastric Content", *European Journal of Biochemistry*. Vol. 78 (1977), pp. 33–39. A general review of the glycoglycerolipid class of molecules is provided in Ishizuka, I., T. Yamakawa, "Glyco-glycerolipids", *New Comprehensive Biochemistry*, Vol. 10 (1985), pp. 101–197. This review covers the occurrence and properties of this class of molecules.

The synthesis of a trisaccharide sulfated glyceroglucolipid homologue has been reported in Ogawa, T., T. Horisaki, "Synthesis of 2-O-hexadecanpyl-1-O-hexadecyl-[α-Glc-6SO₃ Na-(1-6)-α-Glc(1-6)-α-Glc-(1-3)]-sn-glycerol: a proposed structure for the glyceroglucolipids of human gastric secretion and of the mucous barrier of the rat-stomach antrum", *Carbohydrate Research*. Vol. 123 (1983), pp. C1–C4. The synthesis of a sulfated glycerogalactolipid has been reported in Gigg, R., "The Allyl Ether as a Protecting Group in Carbohydrate Chemistry. Part 10. Synthesis of 3-O-(β-D-galactopyranosyl-3-sulfate)-2-O-hexadecanpyl-1-O-hexadecyl-L-glycerol, 'Seminolipid'", *Journal of the Chemical Society, Perkin Transactions* 1, No. 3 (1979), pp. 712–718. Other sulfur containing glycolipids are reviewed in Gigg, R., "Studies on the Synthesis of Sulfur-Containing Glycolipids", *Carbohydrate Sulfates*, American Chemical Society Symposium Series, Vol. 77 (1978), pp. 44–66. This volume also reviews a variety of other types of carbohydrate sulfates and describes their properties and uses.

The adherence of *H. pylori* to triglucosyl monoalkyl-monoacylglycerol sulfate is disclosed in Slomiany, B. L., J. Piotrowski, A. Samanta. K. VanHorn, V. L. N. Murty & A. Slomiany, "*Campylobacter pylori* Colonization Factor Shows Specificity for Lactosylceramide Sulfate and GM3 Ganglioside", *Biochemistry International*, Vol. 19, No. 4 (October, 1989), pp. 929–936. The adherence of *H. pylori* to a sulfated alkylacyl glycerolipid is reported in Lingwood, C. A., H. Law, A. Pellizzari, P. Sherman & B. Drumm, "Gastric Glycerolipid as a Receptor for *Campylobacter pylori*", *The Lancet*. Jul. 29, 1989, pp. 238–241.

It is an object of the subject invention to provide novel methods for treating or preventing gastroduodenal diseases or disorders caused or mediated by *H. pylori*, such as gastritis and peptic ulcer disease.

SUMMARY OF THE INVENTION

The subject invention relates to methods for treating or preventing gastroduodenal diseases or disorders caused by or associated with *H. pylori* comprising administering to a human or lower animal a safe and effective amount of a sulfated glyceroglucolipid having the structure:

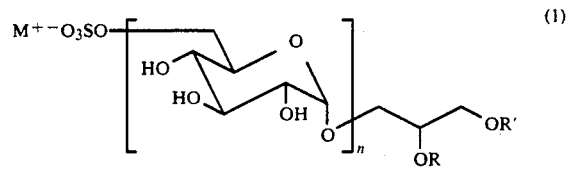

wherein n is an integer of from 1 to about 5, R is hydrogen or $C_1$–$C_{24}$ acyl or alkyl, $R_1$ is hydrogen or $C_1$–$C_{24}$ acyl or alkyl, and $M^+$ is a pharmaceutically-acceptable cationic moiety.

DETAILED DESCRIPTION OF THE INVENTION

The term "alkyl", as used herein, means carbon-containing chains which may be straight, branched or cyclic; and which may be saturated, monounsaturated (e.g., one double or triple bond in the chain), or polyunsaturated (e.g., two or more double bonds in the chain, two or more triple bonds in the chain, one or more double and one or more triple bond in the chain). Preferred alkyl are as noted in this paragraph, unless provided otherwise in particular instances. Preferred alkyl are straight chain. Alkyl groups may be substituted or, preferably, unsubstituted. Preferred substituents are selected from the group consisting of halogen, hydroxy, acyloxy, alkoxy, amino, nitro, aryl, benzyl, aryloxy, trifluoromethyl, heteroaryl and formylamino. More preferred substituents are nonhydrophilic. Especially preferred substituents are selected from the group consisting of aryl, heteroaryl, halogen, trifluoromethyl, and alkoxy.

The term "acyl", as used herein, means —C(O)-alkyl.

The term "aryl", as used herein, means aryl rings which may be mono-, di-, tri-, or unsubstituted. Preferred aryl is as noted in this paragraph, unless provided otherwise in particular instances. Preferred aryls include unsubstituted and substituted phenyl and naphthyl. Preferred substituents include halogen, hydroxy, acyloxy, alkoxy, amino, nitro, phenyl, benzyl, benzyloxy, trifluoromethyl, formal amino and alkyl. Especially preferred substituents include halogen, acyloxy, alkoxy, nitro, phenyl, benzyl, benzyloxy, trifluoromethyl and alkyl.

The term "heteroaryl", as used herein, means aryl rings in which one or more of the carbon atoms of the ring is replaced by nitrogen, oxygen or sulfur. Preferred heteroaryls include purinyl, pyrimidinyl, imidazolyl, furyl, pyridyl, thienyl, pyrrolyl and thiazpyl. Preferred substituents include halogen, hydroxy, acyloxy, alkoxy, aryloxy, amino, nitro, phenyl, benzyl, benzyloxy, trifluoromethyl, formal amino and alkyl. Especially preferred substituents include halogen, acyloxy, alkoxy, aryloxy, nitro, phenyl, benzyl, benzyloxy, trifluoromethyl and alkyl.

The subject invention involves the use of sulfated glyceroglucolipids for treatment or prevention of gastroduodenal diseases or disorders caused by or associated with *H. pylori*, the sulfated glyceroglucolipid having the structure:

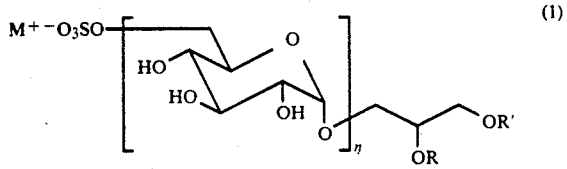

(1)

In Structure (1), n is an integer of from 1 to about 5, preferably from 1 to 4, more preferably 2 or 3, especially 2.

In Structure (1), R is hydrogen or $C_1$–$C_{24}$ acyl or alkyl, more preferably $C_3$–$C_{22}$ acyl or alkyl, more preferably still $C_{10}$–$C_{20}$ acyl or alkyl, still more preferably $C_{12}$–$C_{18}$ acyl or alkyl. Also preferred is R being hydrogen. R is preferably saturated, monounsaturated or diunsaturated, especially with double bonds. Most preferably, R is saturated. R is preferably straight or branched chain, especially straight chain. R is preferably unsubstituted.

In Structure (1), R' is hydrogen or $C_1$–$C_{24}$ acyl or alkyl, preferably $C_3$–$C_{22}$ acyl or alkyl, more preferably $C_{10}$–$C_{20}$ acyl or alkyl, more preferably still $C_{12}$–$C_{18}$ alkyl. R' is preferably saturated, monounsaturated or diunsaturated, especially with double bonds. Most preferably, R' is saturated. R' is preferably straight-chained or branched-chained, especially straightchained R' is preferably unsubstituted.

In Structure (1), M+ is a cationic moiety. Preferred M+ is selected from the group consisting of hydrogen, alkali metal, alkaline metal, ammonium or alkyl-substituted ammonium ions. More preferred M+ are alkali earth metal ions such as lithium, sodium and potassium, especially sodium.

The carbon to which the —OR moiety is bonded in Structure (1) is a chiral center. Therefore, the compound of Structure (1) can have stereospecific structure at this carbon with the structure being the L-form or D-form or mixtures thereof. Preferred stereospecific structures are the racemic mixture, and especially the L-form.

*H. pylori* has been implicated as a cause of or a contributing factor to various chronic disorders of the upper gastrointestinal tract, especially gastritis, gastric ulcer disease and duodenal ulcer disease. The upper gastrointestinal tract, as used herein, is defined as the esophagus, the stomach and the duodenum. Gastritis is, by definition, typified by an inflammation of the stomach mucosa. In practice, though, the disorder is manifested by a broad range of poorly-defined symptoms such as indigestion, heartburn, epigastric pain, nausea, vomiting, anorexia and/or excessive eructation. Peptic ulcers are lesions of the gastric or duodenal mucosa, characterized by loss of tissue.

Sulfated glyceroglucolipids have been found to inhibit the adherence of *H. pylori* to the mocusa of the upper gastrointestinal tract. Adherence of the bacteria to the mucosa is a necessary inilial step in the infection of the gastroduodenal tissue by the bacteria. Inhibition of adherence of *H. pylori* can be determined using the following Test Methods.

Test Method 1

Isolates of *H. pylori* are grown in Brucella broth (Difco) supplemented with 5% fetal bovine serum (Gibco) as described in Morgan, D. R., R. Freedman, C. E. Depew and W. G. Kraft, "Growth of *Campylobacter pylori* in Liquid Media", *Journal of Clinical Microbiology*, Vol. 25 (1987), pp. 2124–2125. Cultures are incubated at 37 C for 24 hours in a gyratory water bath (New Brunswick Scientific) infused with a gas mixture containing 5% oxygen, 10% carbon dioxide, and 85% nitrogen.

To radiolabel bacteria, the growth medium is supplemented with 10 $\mu$Ci/ml D-(6-$^3$H) glucosamine hydrochloride (Amersham). Radiolabeled bacteria are washed 5 times by centrifugation and resuspended in cell culture medium. Viable bacteria are enumerated by a standard plate count technique. Duplicate 10 $\mu$l aliquots are removed for scintillation counting. The specific activity of radiolabeled bacteria is routinely about $0.2-8 \times 10^{-3}$ disintegrations per minute (dpm) per viable bacterium. Less than 7% of the radioactivity is separable from the bacteria by filtration using a 0.45 micron pore size filter.

HeLa cells (human cervical carcinoma cells, ATCC CCL2) are obtained from the American Type Culture Collection. HeLa cells are grown in Eagle's Minimal Essential Medium with Earle's salts and 25 mM Hepes (Gibco) supplemented with 5% fetal bovine serum and 2 mM glutamine (Gibco). Cells are incubated at 37° C. in a humidified atmosphere containing 5% carbon dioxide.

Cultured HeLa cells are seeded at $5 \times 10^4$ per well in 24-well culture plates. Wells containing medium only (without cells) serve as controls for nonspecific binding. After 18-24 hours incubation, the medium is aspirated and 0.5 ml of radiolabeled bacteria (typically $2-5 \times 10^7$ colony forming units (cfu)) is added to each well. After 3 hours incubation as above, the medium is aspirated and wells are washed 3 times to remove nonadherent bacteria. Washings consist of addition of 1 ml culture medium followed by agitation for 30 seconds. Microscopic observations are made both before and after washing. Cells with adherent bacteria are lysed by addition of 0.5 ml sodium dodecyl sulfate (0.5%) to each well. After incubation at 37° C. for 60 minutes, 0.25 ml is removed for scintillation counting.

Samples are counted in ml BIO-SAFE II ® biodegradable counting cocktail (Research Products International) in a TRI-CARB® 2000 Ca liquid scintillation counter (Packard). Dpm bound to wells without cells are subtracted from those bound to wells containing cells to determine the number of bacteria bound per well.

For inhibition studies, a test compound is diluted in cell culture medium to four times the desired final concentration. Radiolabeled *H. pylori* (1 ml), test inhibitor (1 ml), and additional cell culture medium (2 ml) are then mixed and incubated 15–30 minutes at room temperature. Aliquots (0.5 ml) of bacteria and test compound are added to wells with and without HeLa cells. Bacterial adherence is quantitated as described above and expressed as the number of bacteria bound per well. Adherence of bacteria in the absence of a test compound serves as a control. The percentage inhibition of adherence is calculated using the following equation.

$$\frac{\text{control adherence} - \text{adherence in the presence of test compound}}{\text{control adherence}} \times 100$$

Adverse effects of certain test compounds on bacteria or HeLa cells are determined in control experiments. A standard plate count technique is used to enumerate viable bacteria immediately after dilution with the test compound and after 3 hours incubation in the presence of the test compound. Bacteria incubated and enumerated similarly in the absence of any test compound serve as the control. In addition, HeLa cells incubated in the presence of a test compound (without bacteria) are observed microscopically. A subjective evaluation of changes in cell attachment to the substratum or decreases in cell surface area is made. Only concentrations of test compounds which do not affect bacterial viability or decrease HeLa cell attachment are used for inhibition studies.

Test Method 2

Gnotobiotic piglets are derived by cesarean section and maintained under germ-free conditions as described in Krakowka, S., D. R. Morgan, W. G. Kraft, and R.D. Leunk, "Establishment of Gastric *Campylobacter pylori* Infection in the Neonatal Gnotobiotic Piglet", *Infection and Immunity*, Vol. 55 (1987), pp. 2789–2796. On day 3 of life, piglets are challenged with *H. pylori*. Half of the piglets (control group) receive bacteria suspended in phosphate-buffered saline (PBS), pH 7.2. The other half of the piglets (experimental group), housed in a separate isolator, receive bacteria suspended in PBS containing the test compound. The number of viable bacteria in each challenge innoculum is determined using a standard plate count technique. Six hours after challenge, piglets are sacrificed and the level of bacterial colonization in gastric tissue is determined. The lower esophagus and pylorus are ligated and the stomach is excised aseptically. The stomach is divided in half longitudinally, weighed, and the gastric mucosa from one half is aseptically scraped into sterile Brucella broth using a scalpel. The weight of gastric mucosa collected is calculated by subtracting the weight of one half stomach after scraping of the mucosa from its initial weight.

Gastric mucosal scrapings are homogenized in Brucella broth using a Ten Broek tissue grinder and the total volume of homogenate is recorded. The number of viable bacteria in mucosal homogenates is determined using a standard plate count technique. Gastric mucosal homogenates are serially diluted in Brucella broth and aliquots are plated on Trypticase Soy Agar supplemented with 5% sheep blood (BBL, Cockeysville, Md.). The level of bacterial colonization for each animal is expressed as the logarithm of the cfu per one half stomach and as the logarithm of the cfu per gram gastric mucosa. Group means are calculated for the experimental and control groups and compared statistically using a t test.

When used to treat or prevent gastroduodenal disorders, the quantity of the sulfated glyceroglucolipid administered is preferably from about 0.1 mg/kg to about 500 mg/kg, more preferably from about 1 mg/kg to about 100 mg/kg, more preferably still from about 2 mg/kg to about 30 mg/kg, still more preferably from about 5 mg/kg to about 15 mg/kg. These quantities are preferably administered from about 1 to about 4 times daily, more preferably 2 or 3 or especially 4 times daily. A dose is preferably administered from about 0 to about 2 hours before meals, more preferably from about ½ hour to about 1 hour before meals. A dose is also preferably administered at bedtime.

The subject invention includes the use of sulfated glyceroglucolipids in combination with antimicrobial agents for treatment or prevention of gastroduodenal diseases or disorders caused by or associated with *H. pylori*. The sulfated glyceroglucolipid can be administered concomitant with or subsequent to a course of therapy with an antimicrobial agent. Antimicrobial agents and courses of therapy thereof which are useful in combination with the sulfated glyceroglucolipids are disclosed under the categories of "Antibacterials & Antiseptics" and "Antibiotics" in *Physicians' Desk Reference*. E. R. Barnhart Publisher, 44th Edition (1990), and *Physicians' Desk Reference for Nonprescription Drugs*. E. R. Barnhart Publisher, 11th Edition (1990) (herein collectively "PDRs"), which are incorporated by reference herein. Preferred non-limiting examples of antimicrobial agents which can be used in combination with the sulfated glyceroglucolipids include antimicrobials of the following classes: penicillins, cephalosporins, tetracyclines, bismuth salts, macrolides, imidazoles, nitrofurans, rifampins, quinolones, and aminoglycosides; especially the following antimicrobials: ampicillin, amoxicillin, tetracycline, metronidazole, bismuth subsalicylate, colloidal bismuth subcitrate, bismuth subgallate, bismuth subnitrate, nitrofurantoin, furazolidone, erythromycin, cephalothin, cefaclor, cefixime, rifampin, doxycycline, norfloxicin, ciprofloxacin, enoxacin, amikacin, gentamycin, kanamycin, chloramphenicol and neosporin.

The subject invention includes the use of sulfated glyceroglucolipids in combination with other anti-ulcer medications for treatment or prevention of gastroduodenal diseases or disorders caused by or associated with *H. pylori*. The sulfated glyceroglucolipids can be administered concomitant with or subsequent to a course of therapy with the other anti-ulcer medication. Anti-ulcer medications and courses of therapy which can be used in combination with the sulfated glyceroglucolipids are disclosed under the categories of "Histamine $H_2$ Receptor Antagonists", "Antacids", "Duodenal Ulcer Adherent Complex" and "Prostaglandin Analog" in the PDRs. Preferred, non-limiting examples of such other anti-ulcer medications include cimetidine, ranitidine, omeprazole, sucralfate, famotidine, nizatidine, magnesium hydroxide, aluminum hydroxide, simethicone, magaldrate and calcium carbonate.

Another aspect of the present invention is pharmaceutical compositions intended for peroral administration comprising a sulfated glyceroglucolipid as defined hereinbefore and a pharmaceutically-acceptable carrier.

The term "pharmaceutically-acceptable carrier", as used herein, means one or more compatible solid or liquid filler diluents or encapsulating substances which are suitable for peroral administration to a human or lower animal. The term "compatible", as used herein, means that the components of the pharmaceutical compositions are capable of being commingled with the sulfated glycerolipid, and with each other in a manner such that there is no interaction which would substantially reduce the pharmaceutical efficacy of the pharmaceutical composition under ordinary usage situations. Pharmaceutically-acceptable carriers must, of course, be of sufficiently high purity and sufficiently low toxicity to render them suitable for peroral administration to the human or lower animal being treated.

Some examples of substances which can serve as pharmaceutically-acceptable carriers are sugars, such as lactose, glucose and sucrose; starches, such as corn starch and potato starch; cellulose and its derivatives, such as sodium carboxymethylcellulose, ethyl cellulose, cellulose acetate; powdered tragacanth; malt; gelatin; talc; solid lubricants, such as stearic acid, magnesium stearate; calcium sulfate; vegetable oils such as peanut oil, cottonseed oil, sesame oil, olive oil, corn oil and oil of theobroma; polyols such as propylene glycol, glycerin, sorbitol, mannitol and polyethylene glycol; alginic acid; emulsifiers; wetting agents such as sodium lauryl sulfate; coloring agents; flavoring agents; excipients; tableting agents; stabilizers; anti-oxidants; and preservatives.

The compositions of the subject invention are preferably in dosage unit form, each dosage unit comprising from about 1 mg to about 5 g, more preferably from about 10 mg to about 2 g, more preferably still from about 100 mg to about 1 g, still more preferably from about 250 mg to about 500 mg, of the sulfated glyceroglucolipid.

Synthesis of Sulfated Glyceroglucolioids

The following non-limiting examples are exemplary of the methods used to synthesize sulfated glyceroglucolipids and intermediates thereto.

Chemicals used in the examples are available from Sigma Chemical Company or Aldrich Chemical Company, except for anhydrous silver perchlorate obtainable from Pfaltz & Bauer, Inc. Reactions are performed under anhydrous conditions, using freshly distilled solvents under argon atmosphere in oven- or flame-dried glassware, unless described otherwise. All solvents are distilled under nitrogen atmosphere. Dichloromethane and toluene are distilled from calcium hydride, whereas diethyl ether and tetrahydrofuran are distilled from sodium-benzophenone. Reagent grade N,N-dimethylformamide and methanol are dried over 4A molecular sieves. The absolute ethanol used is not dried. The reaction temperatures are measured externally and are uncorrected.

The reactions are monitored using analytical thin layer chromatography (TLC) with plates precoated with silica or $C_{18}$ reverse-phase bond silica (250-micron thickness) with or without fluorescent indicators. The developed TLC plates are visualized with UV light and/or immersion in 10% $H_2SO_4$ in ethanol or 7% polyphosphomolybdic acid in ethanol followed by heating on a hot plate. Column chromatography is carried out on either Merck silica gel 60 or Baker $C_{18}$ a reverse-phase bonded silica.

EXAMPLE 1

Phenyl 2,3,4,6-Tetra-O-acetyl-1-thio-$\beta$-D-glucopyranoside (2). $\alpha$-D-Glucose pentaacetate (1, 100 g) and thiophenol (32 mL) are dissolved in $CH_2Cl_2$ (850 mL). After cooling to 0° C., $SnCl_4$ (18 mL) is added and the reaction is allowed to come to room temperature. After stirring overnight, the reaction is complete (TLC, silica, 10% EtOAc in $CH_2Cl_2$). The reaction is diluted with $CH_2Cl_2$ (400 mL) and the solution is added to a mixture of ice and 10% $NaHCO_3$ (500 mL). After filtration through celite, the resulting solution is added to a separatory funnel. The aqueous layer is discarded and the $CH_2Cl_2$ portion is washed successively with 10% $NaHCO_3$ (2×200 mL), water (2×200 mL) and brine (300 mL). The $CH_2Cl_2$ solution is then dried over $MgSO_4$ and filtered. The $CH_2Cl_2$ is removed in vacuo and the solid obtained is recrystallized (EtOAc/Hexane). The white crystals obtained (94 g) are phenyl 2,3,4,6-tetra-O-acetyl-1-thio-$\beta$-D-glucopyranoside (2) and a small amount of the corresponding $\alpha$-anomer (ca. 20:1).

Phenyl ]-Thio-$\beta$-D-glucopyranoside (3). To a solution of 2 (50 g) in MeOH (570 mL) at 0° C. is added NaOMe (3 g). The reaction is allowed to come to room temperature overnight. TLC analysis (silica, 7% MeOH in $CH_2Cl_2$) indicates that the reaction is complete. Highly acidic ion-exchange resin (Amberlyst-15, 5 g) is added and the reaction is stirred until pH 7 is attained. The resin is then filtered off and the MeOH is removed in vacuo. The white solid obtained (30 g) is phenyl 1-thio-$\beta$-D-glucopyranoside (3) and a small amount of the corresponding $\alpha$-anomer (ca 20:1).

Phenyl 6-O-(tert-Butyldiohenylsilyl)-1-thio-$\beta$-D-glucopyranoside (4). Imidazole (32 g) is added to a solution of 3 (30 g) in DMF (225 mL). After cooling to 0° C., tert-butyldiphenylsilyl chloride (34 g) is added. The reaction is allowed to come to room temperature overnight, whereupon TLC analysis (silica, 10% MeOH in $CH_2Cl_2$) indicates that the reaction is complete. MeOH (30 mL) is added and the reaction is stirred for an additional 30 minutes. The solvents are then removed in vacuo (40° C., 10 mm Hg). The residue is dissolved in EtOAc (500 mL) and washed successively with water (2×100 mL) and brine (2×100 mL). The EtOAc solution is then dried ($MgSO_4$) and filtered. Removal of the EtOAc in vacuo provides a syrup which is subjected to flash column chromatography (silica, 5% EtOAc in hexane) to provide phenyl 6-O-(tert-butyldiphenylsilyl)-1-thio-$\beta$-D-glucopyranoside (4, 51 g).

Phenyl 6-O-(tert-Butyldiphenylsilyl)-2,3,4-tri-O-benzyl-1-thio-$\beta$-D-glucooyranoside (5). To a cooled (0° C.) solution of 4 (4.9 g) in THF (26 mL) is added sodium hydride (2.3 g of a 60% suspension in oil). The mixture is allowed to come to room temperature. After recooling to 0° C., benzyl bromide (10 g) is added. The reaction is again allowed to come to room temperature and tetra-n-butylammonium iodide (0.2 g) is added. The reaction is heated to reflux and allowed to stir until TLC analysis (silica, 5% EtOAc in hexane) indicates reaction completion (ca. 72 hrs.). The reaction is cooled to 0° C., quenched with methanol (50 mL) and allowed to come to room temperature. After stirring for 20 minutes at room temperature, water (50 mL) and EtOAc (250 mL) are added. The mixture is transferred to a separatory funnel and the organic portion is washed successively with water (2×100 mL) and 0.1M HCl solution (2×100 mL). The combined aqueous washes are then extracted with EtOAc (50 ml). The combined organic portions are then washed with brine (2×100 mL), dried over MgSO$_4$ and filtered. After removal of the EtOAc 1D vacuo. The syrup obtained is subjected to flash column chromatography (silica, 50% EtOAc in hexane) to obtain phenyl 6-O-(tert-butyldiphenylsilyl)-2,3,4-tri-O-benzyl-1-thio-β-D-glucopyranoside (5, 4.8 g).

6-O-(tert-Butyldiohenylsilvl)-2,3,4-tri-O-benzyl-α-and β-D-glucopyranosyl fluoride (6 and 7). To a cooled (−15° C.) solution of 5 in CH$_2$Cl$_2$ (30 mL) is added N-bromosuccinimide (1.91 g) and diethylaminosulfur trifluoride (2.29 mL). The reaction is allowed to warm to room temperature overnight whereupon TLC analysis (silica, 5% EtOAc in hexane) indicates reaction completion. The reaction mixture is added to a stirred slurry of ice and 10% NaHCO$_3$ (500 g). The mixture is transferred to a separatory funnel and the CH$_2$Cl$_2$ is washed with water (3×100 mL) and brine (100 mL). After drying over MgSO$_4$ and filtration, the CH$_2$Cl$_2$ is removed in vacuo. The syrup obtained is subjected to flash column chromatography (silica, 5% EtOAc in hexane) to provide a mixture of 6-O-(tert-butyldiphenylsilyl)-2,3,4-tri-O-benzyl-α- and β-D-glucopyranosyl fluorides (6 and 7, 3.6 g).

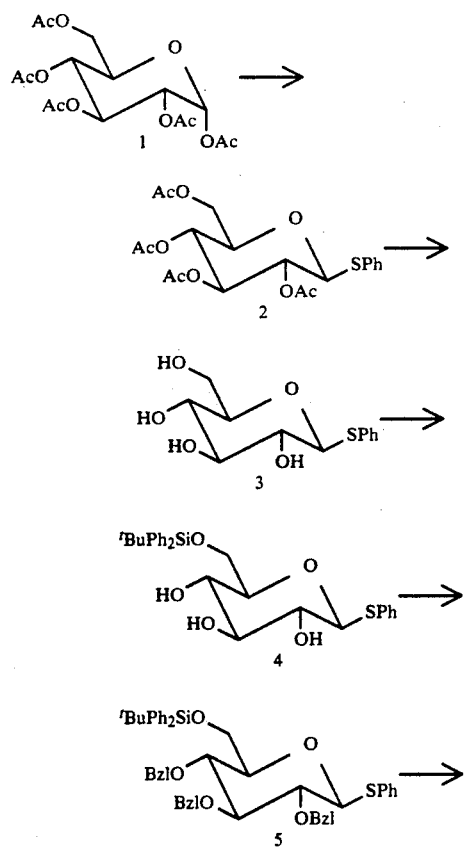

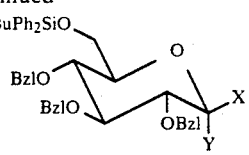

6 X = H, Y = F
7 X = F, Y = H

L-1-O-Hexadecyl-2,3-O-isopropylidene-sn-glycerol (9) and L-1-O-Hexadecyl-sn-glycerol (10). L-2,3-O-Isopropylidene-sn-glycerol (8, 13 g) in THF (190 mL) is cdoled to 0° C. and NaH (7.6 g of a 60% suspension in oil) is added. After warming to room temperature and recooling to 0° C., bromohexadecane (58 mL) is added to the mixture. After warming to room temperature, tetra-n-butylammonium iodide (1.8 g) is added and the mixture is heated to 60° C. After stirring overnight, TLC analysis (silica, 40% EtOAc in hexane) indicates that the reaction is complete The reaction is cooled to room temperature and methanol (10 mL) is added. After stirring for 30 minutes, the reaction is diluted with ether (75 mL) and water (25 mL). After stirring for an additional 30 minutes, EtOAc (75 mL) is added and the mixture is transferred to a separatory funnel. After washing the organic portion with water (2×50 mL), 0.1N HCl (2×50 mL) and brine (2×50 mL), the aqueous layers are combined and extracted once with ether (50 mL). The combined organic layers are then dried over MgSO$_4$ and filtered. The solvents are removed in Vacuo to obtain crude L-1-O-hexadecyl-2,3-O-isopropylidene-sn-glycerol (9). Methanol (300 mL) and highly acidic ion exchange resin (Amberlyst-15, 30 mL) are added to the crude mixture. The reaction is heated to 50° C. and stirred until TLC analysis (silica, 40% EtOAc in hexane) indicates reaction completion. The mixture is then cooled and the resin is filtered off and washed with ether (50 mL). After the addition of CCl$_4$ (100 mL), the solvent mixture is evaporated in Vacuo. Chloroform (100 mL) is added to the solid product and then evaporated in vacuo. Several portions of chloroform are thus added and evaporated (2x). Finally, the solid obtained is recrystallized (chloroform/hexane) and the crystals obtained are filtered and washed with cold hexane (50 mL). The recrystallization process is then repeated on the mother liquor. The first and second crops are combined and dried over P$_2$O$_5$ in vacuo to obtain L-1-O-hexadecyl-snglycerol (10, 25 g).

L-3-O-tert-Butyldiphenylsilyl-1-O-hexadecvl-sn-glycerol (11). To a solution of 10 (15 g) in DMF at 0° C. is added imidazole (6.8 g) and tert-butyldiphenylsilyl chloride (13.7 mL). The reaction is allowed to come to room temperature and is stirred until TLC analysis (silica, 5% EtOAc in hexane) indicates reaction completion. Methanol (5 mL) is added and the mixture is allowed to stir overnight. The reaction is then diluted with ether (600 ml) and water (100 mL) and transferred to a separatory funnel. The organic portion is washed with water (2×100 mL) and then the water layers are combined and extracted with ether (50 mL). The combined organic layers are then washed with brine (2×100 mL) and dried over MgSO$_4$. After filtration, the solvents are removed in vacuo and the syrup obtained is subjected to flash column chromatography (silica, 5% EtOAc in hexane) to obtain L-3-O-tert-butyldiphenylsilyl-1-O-hexadecyl-sn-glycerol (11, 24 g).

L-3-O-tert-Butyldiphenylsilyl-1-O-hexadecyl-2-O-palmitoyl-sn-glycerol (12). To a solution of CH$_2$Cl$_2$ (24 g) in CH$_2$Cl$_2$(215 mL) at 0° C. is added 4-dimethylaminopyridine (7 g) and palmitpyl chloride (10 mL). The reaction is stirred overnight whereupon TLC analysis (silica, 5% EtOAc in hexane) indicates that the reaction is complete CH$_2$Cl$_2$ (600 mL) and water (100 mL) are added and the mixture is transferred to a separatory funnel. The CH$_2$Cl$_2$ layer is washed with water (2×100 mL) and brine (100 mL) and dried over MgSO$_4$. After filtration, the solvent is removed in vacuo to obtain a syrup. The syrup is subjected to flash column chromatography (silica, 5% EtOAc in hexane) to obtain L-3-O-tert-butyldiphenylsilyl-1-O-hexadecyl-2-O-palmitpyl-sn-glycerol (12, 32 g).

L-1-O-Hexadecyl-2-O-palmitoyl-sn-glycerol (13). To a solution of 12 (7.7 g) in THF (50 mL) at 0° C. is added HF-pyridine complex (6 mL). The reaction is allowed to come to room temperature overnight whereupon TLC analysis (silica, 7% EtOAc in hexane) indicates reaction completion. The reaction is diluted with ether (200 mL), and 10% NaHCO$_3$ solution is added until effervescence ceases. The mixture is then quickly transferred to a separatory funnel and washed with 10% NaHCO$_3$ (4×200 mL) and brine (2×200 mL). The solution is dried briefly over MgSO$_4$ and filtered. The solvents are then removed in vacuo at room temperature and the residue obtained is immediately crystallized (EtOAc/hexane) to obtain L-1-O-hexadecyl-2-O-palmitpyl-snglycerol (13, 4 g). The compound is then stored desiccated in a freezer until used.

6-O-(tert-Butyldiphenylsilyl)-2,3,4-tri-O-benzyl-α-D-glucopyranosyl-(1-3')-L-1-O-hexadecvl-2-O-palmitoyl-sn-glycerol (14). A mixture of SnCl- (1.9 g) and AgClO$_4$ (2 g) is azeotropically dried with toluene (2×50 mL) in vacuo. Ether (100 mL) and 4A molecular sieves (3 g, flame-dried) are added to this mixture and the solution is cooled to −20° C. The mixture of glucopyranosyl fluorides 6 and 7 (3.8 g) and L-1-O-hexadecyl-2-O-palmitpyl-sn-glycerol (13. 3 g) are separately azeotropically dried with toluene (2×50 mL). Glycerol derivative 13 in ether (40 mL) is added to the catalyst mixture, followed by addition of the glycosyl fluoride mixture (6 and 7) in ether (40 mL). The reaction temperature is maintained at −20° C. overnight, whereupon TLC analysis (silica, 5% EtOAc in hexane) indicates that the reaction is complete. The cooling bath is removed and the reaction is diluted with ether (200 mL). The mixture is filtered through celite and the filtrate is transferred to a separatory funnel. The organic portion is washed successively with 10% NaHCO$_3$ (2×10 mL) and brine (2×70 mL), dried over MgSO$_4$, and filtered. After evaporation of the solvents in vacuo. the residue obtained is subjected to flash column chromatography (silica, 5% EtOAc in hexane) to obtain 6-O-(tert-butyldiphenylsilyl)-2,3,4-tri-O-benzyl-α-D-glucopyranosyl-(1-3')-L-1-O-hexa-decyl-2-O-palmitpyl-sn-glycerol (14, 3.8 g) with a high α-glycoside selectivity.

2,3,4-Tri-O-benzyl-β-D-glucopyranosyl-(1-3')-L-1-O-hexadecyl-2-O-palmitpyl-sn-glycerol (15). To a solution of glycoside 14 (3.7 g) in THF (6 mL) at 0° C. is added tetra-n-butylammonium fluoride (3.6 mL of a 1M solution in THF). The reaction is maintained at 0° C. for one hour and is then allowed to come to room temperature overnight. TLC analysis (silica, 20% EtOAc in hexane) of the reaction mixture indicates that the reaction is complete. The reaction is diluted with ether (150 mL) and the mixture is transferred to a separatory funnel and washed successively with 10% NaHCO$_3$ (2×40 mL) and brine (2×40 mL). The organic extract is then dried over MgSO$_4$ and filtered. The solvents are evaporated in vacuo to provide a residue which is subjected to flash column chromatography (silica, 20% EtOAc in hexane) to provide 2,3,4-tri-O-benzyl-β-D-glucopyranosyl-(1-3')-L-1-O-hexadecyl-2-O-palmitpyl-sn-glycerol (15, 2.6 g).

Sodium 6-O-Sulfate-2,3,4-tri-O-benzyl-α-D-glucopyranosyl-(1-3')-L-1-O-hexadecyl-2-O-palmitoyl-sn-glycerol (16). To a solution of glycoside 15 (0.78 g) in ether (3 mL) is added 4-dimethylaminopyridine (0.19 g) and sulfur trioxide-pyridine complex (1.3 g). The reaction is allowed to stir overnight whereupon TLC analysis (silica, 5% methanol in ether) indicates that the reaction is complete. The reaction is diluted with ether (200 mL), water (100 mL) and 2N HCl (150 mL). The organic portion of the resulting mixture is washed successively with L brine (50 mL) and 10% NaHCO$_3$ (50 mL). The ether solution is then dried over Na$_2$SO$_4$ and filtered. The solvent is removed in vacuo to provide sodium 6-O-sulfate-2,3,4-tri-O-benzyl-α-D-glucopyranosyl-(1-3')-L-1-O-hexadecyl-2-O-palmitpyl-sn-glycerol 16 (0.85 g) which is carried on to the next step without further purification.

Sodium 6-O-Sulfate-β-D-glucooyranosyl-(1-3')-L-1-O-hexadecyl-2-O-Dalmitpyl-sn-glycerol (17). To a solution of sulfate 16 (0.8 g) in methanol (8 mL) is added palladium hydroxide on carbon (Pearlman's catalyst, 0.8 g). The reaction is evacuated and flushed with argon (5 x) using a three-way stopcock. The system is then evacuated and flushed with hydrogen (5 x). A balloon filled with hydrogen is then attached to one of the arms of the three-way stopcock and the reaction is stirred at room temperature for 5 days. During this period, the hydrogen balloon is refilled several times. TLC analysis (silica, 75:25:4, CHCl$_3$:MeOH:H$_2$O) is used to monitor the reaction and, upon completion, the system is evacuated and flushed with argon (5 x). The methanol solution is filtered through a millipore filter to remove the catalyst and then the solvent is removed in Vacuo. The residue obtained is subjected to low pressure column chromatography (C$_{18}$-reverse-phase bonded silica, 30% water in isopropanol) to provide sodium 6-O-sulfate-β-D-glucopyranosyl-(1-3')-L-1-O-hexadecyl-2-O-palmitoyl-sn-glycerol (17, 0.5 g).

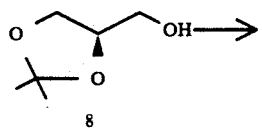

8

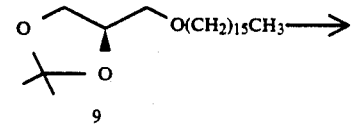

9

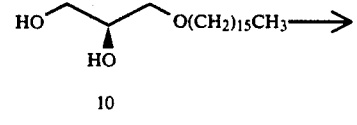

10

-continued

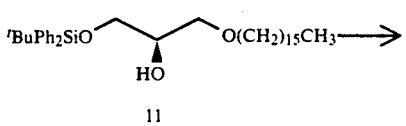

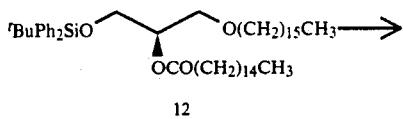

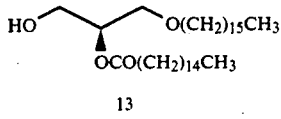

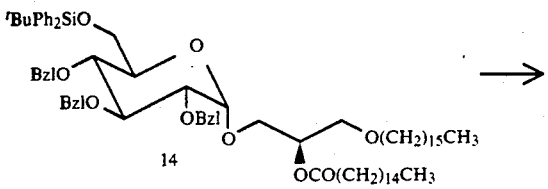

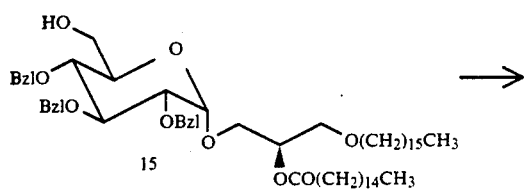

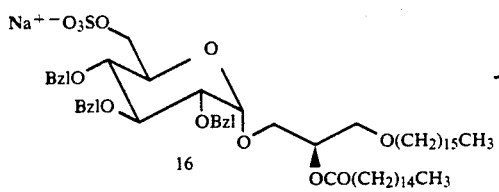

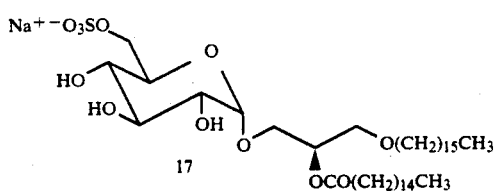

EXAMPLE 2

6-O-(tert-Butyldiphenylsilyl)-2,3,4-tri-O-benzvl-α-D-glucopyranosyl-(1-6)-2,3,4-tri-O-benzvl-α-D-glucopyranosyl-(1,3')-L-1-O-hexadecyl-2-O-palmitoyl-sn-glycerol (18). A mixture of SnCl₂ (0.51 g) and AgClO₄ (0.56 g) is azeotropically dried with toluene (2×50 mL) in vacuo. Ether (30 mL) and 4A molecular sieves (1 g, flame-dried) are added to this mixture and the solution is cooled to −20° C.. The mixture of glucopyranosyl fluorides 6 and 7 (1.1 g) and glycoside 15 (1.5 g) are separately azeotropically dried with toluene (2×50 mL). Glycoside 15 in ether (10 mL) is added to the catalyst mixture, followed by addition of the glycosyl fluoride mixture (6 and 7) in ether (10 mL). The reaction temperature is maintained at −20° C. overnight, whereupon TLC analysis (silica, 5% EtOAc in hexane) indicates that the reaction is complete. The cooling bath is removed and the reaction is diluted with ether (100 ml). The mixture is filtered through celite and the filtrate is transferred to a separatory funnel. The organic portion is washed successively with 10% NaHCO₃ (2×40 mL) and brine (2×40 mL), dried over MgSO₄, and filtered. After evaporation of the solvents in vacuo. The residue obtained is subjected to flash column chromatography (silica, 5% EtOAc in hexane) to obtain 6-O-(tert-butyldiphenylsilyl)-2,3,4-tri-O-benzyl-α-D-glucopyrano-syl-(1-6)-2,3,4-tri-O-benzyl-β-D-glucopyranosyl-(1-3')-L-1-O-hexadecyl-2-O-palmitoyl-sn-glycerol (18. 1.8 g) with a high α-glycoside selectivity.

2,3,4-Tri-O-benzyl-β-D-glucopyranosyl-(1-6)-2,3,4-tri-O-benzyl-a-D-glucopyranosyl-(1-3')-L-1-O-hexadecyl-2-O-palmitoyl-sn-glycerol (19). To a solution of glycoside 18 (1.9 g) in THF (3 mL) at 0° C. is added tetra-ⁿbutylammonium fluoride (1.4 mL of a 1M solution in THF). The reaction is maintained at 0° C. for one hour and is then allowed to come to room temperature overnight. TLC analysis (silica, 20% EtOAc in hexane) of the reaction mixture indicates that the reaction is complete. The reaction is diluted with ether (100 mL) and the mixture is transferred to a separatory funnel and washed successively with 10% NaHCO₃ (2×50 mL) and brine (2×50 mL). The organic extract is then dried over MgSO₄ and filtered. The solvents are evaporated in vacuo to provide a residue which is subjected to flash column chromatography (silica, 20% EtOAc in hexane) to provide 2,3,4-tri-O-benzyl-α-D-glucopyranosyl-(1-6)-2,3,4-tri-O-benzyl-α-D-glucopyranosyl-(1-3')-L-1-O-hexadecyl-2-O-palmitoyl-sn-glycerol (19, 1.4 g).

Sodium 6-O-Sulfate-2,3,4-tri-O-benzyl-α-D-glucopyranosyl(1-6)-2,3,4-tri-O-benzyl-α-D-glucopyranosyl-(1-3')-L-1-O-hexadecyl-2-O-palmitoyl-sn-glycerol (20). To a solution of glycoside 19 (0.8 g) in DMF (5 mL) is added sulfur trioxide-pyridine complex (0.8 g) in DMF (20 mL). The reaction is allowed to stir L overnight whereupon TLC analysis (silica, 10% methanol in CH₂Cl₂) indicates that the reaction is not complete. More sulfur trioxide-pyridine complex (0.5 g) in DMF (6.5 mL) is added and the reaction is again allowed to stir overnight. TLC analysis (silica, 10% methanol in CH₂Cl₂) indicates that the reaction is complete, whereupon methanol (5 mL) is added and the reaction is allowed to stir for 20 minutes. The solvents are then removed in vacuo and the residue obtained is dissolved in CHCl₃ (35 mL) and washed with water (2×50 ml). The CHCl₃ is then removed in vacuo and the residue obtained is then subjected to ion-exchange chromatography (IR-120 sodium form, 10% methanol in CHCl₃) to provide sodium 6-O-sulfate-2,3,4-tri-O-benzyl-β-D-glucopyranosyl-(1-6)-2,3,4-tri-O-benzyl-α-D-glucopyranosyl-(1-3')-L-1-O-hexadecyl-2-O-palmitoyl-sn-glycerol 20 (0.7 g) which is carried on to the next step without further purification.

Sodium 6-O-Sulfate-β-D-glucopyranosyl-(1-6)-α-D-gluco-pyranosyl-(1-6)-L-1-O-hexadecyl-2-O-palmitoyl-sn-glycerol (21). To a solution of sulfate 20 (0.41 g) in ethanol (100 mL) is added palladium hydroxide on carbon (Pearlman's catalyst, D. 2 g). The mixture is placed in a rocking autoclave apparatus. The apparatus is evacuated and charged with hydrogen (300 psi). The reaction is allowed to proceed at room temperature for 48 hours, whereupon TLC alanysis (silica, 70:30:4, CHCl$_3$:MeOH:H$_2$O) indicates that the reaction is complete. The system is evacuated and flushed with helium. The ethanol solution is filtered through glass fiber filter paper to remove the catalyst and then the solvent is removed in vacuo. The residue obtained is subjected to low pressure column chromatography (C$_{18}$-reverse phase bonded silica, 30% water in isopropanol) to provide sodium 6-O-sulfate-α-D-glucopyranosyl-(1-6)-α-D-glucopyranosyl-(1-3')-L-1-O-hexadecyl-2-O-palmitoyl-sn-glycerol (21, 0.12 g).

prepared by coupling disaccharide alcohol 19 with glycosyl fluorides 6 and 7 under conditions similar to those which are used for the preparation of disaccharide 18. Desilation, sulfation and debenzylation, as described for the preparation of compounds 19, 20 and 21, respectively, provides alcohol 23, sulfate 24 and, finally, the trisaccharide sulfated glyceroglucolipid homologue (25), respectively. Similarly, tetrasaccharide 26 may be prepared by coupling disaccharide alcohol 23 with glycosyl fluorides 6 and 7 under conditions similar to those

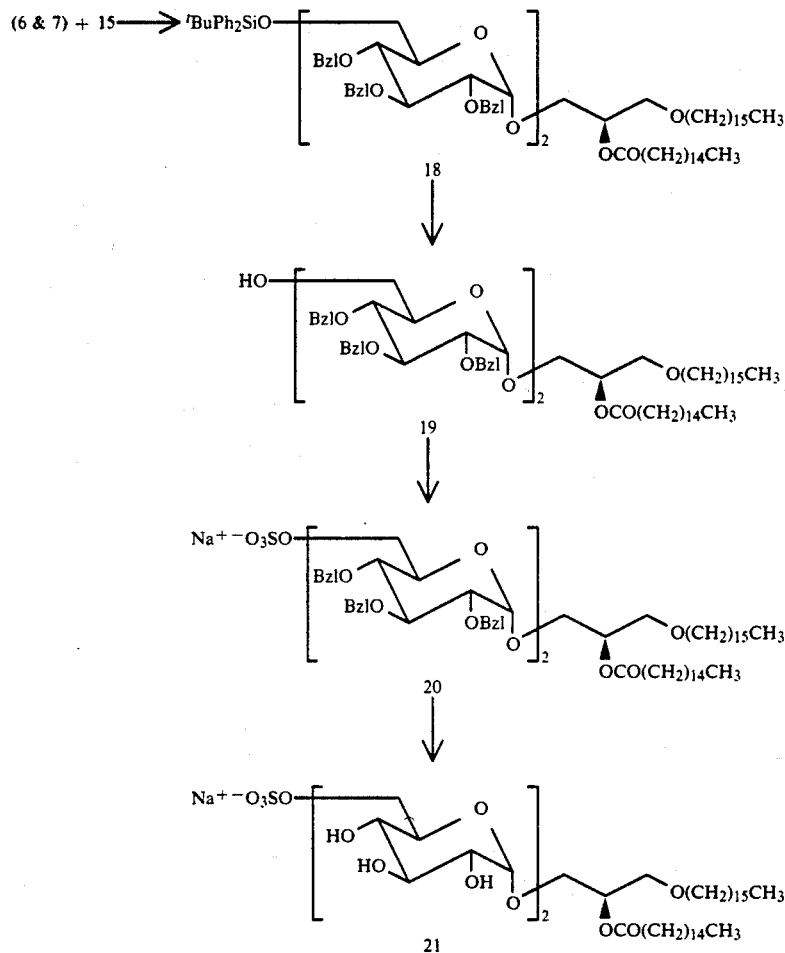

EXAMPLES 3 and 4

Preparation of Higher Homologous

Higher SGGL homologues (25 and 29) are prepared by reiteration of the processes described for the synthesis of the mono and disaccharide homologues (17 and 21 respectively). For example, trisaccharide 22 may be which are used for the preparation of disaccharide 18. Desilation, sulfation and debenzylation, as described for the preparation of compounds 19, 20 and 21. respectively, provides alcohol 27, sulfate 28 and, finally, the tetrasaccharide sulfated glyceroglucolipid homologue (29), respectively.

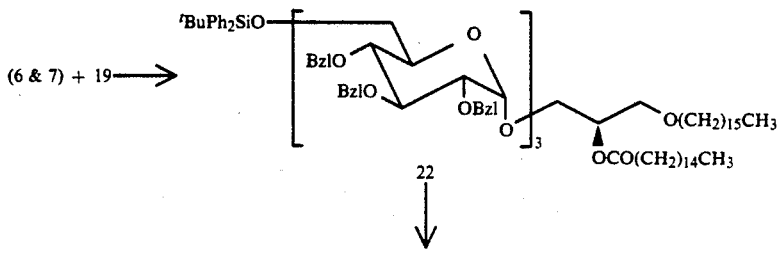

-continued
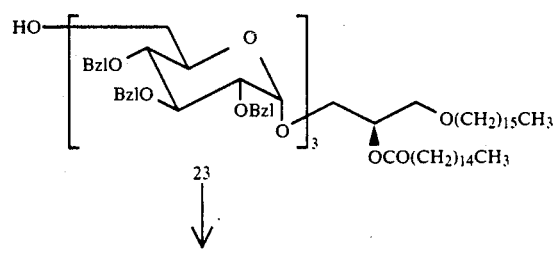
↓ 23
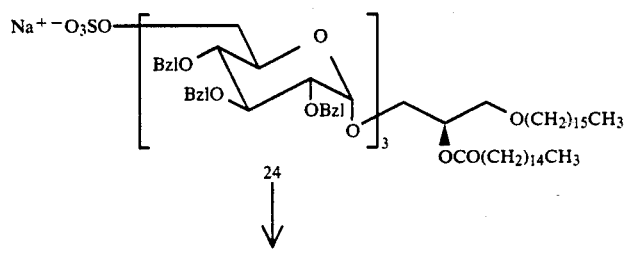
↓ 24
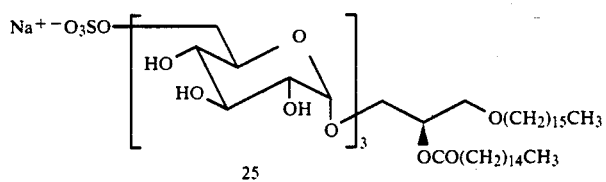
25
(6 & 7) + 23 →
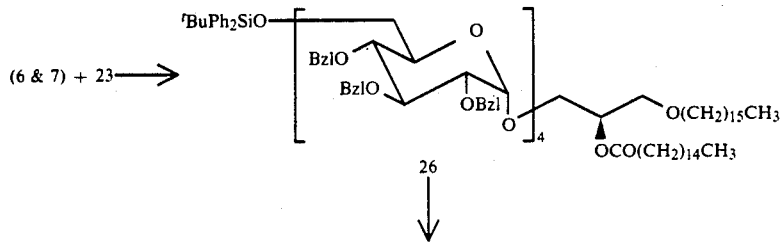
↓ 26
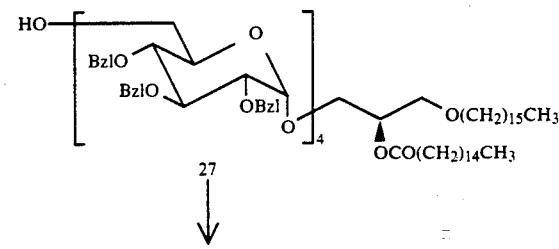
↓ 27
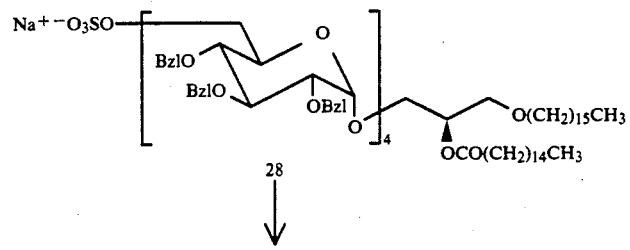
↓ 28
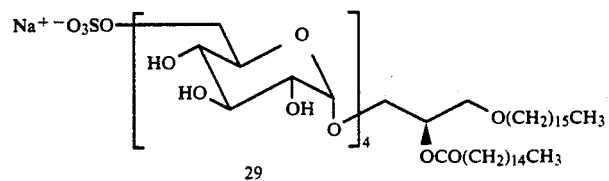
29

The following non-limiting examples are exemplary of the pharmaceutical compositions of the subject invention.

EXAMPLE 5

Compound 21 of Example 2 is admixed with fumed silica (at 0.1%) and magnesium stearate (at 0.5%). Hard gelatin capsule shells are filled by conventional means such that each capsule contains 500 mg of compound 21.

EXAMPLE 6

350 mg of compound 25 of Example 3, mannitol (675 mg), microcrystalline cellulose (75 mg), corn starch (30 mg), calcium stearate (22 mg), and flavor, are admixed and compressed by conventional means to form a chewable tablet.

The following non-limiting examples are exemplary of the methods of treatment and prevention of gastrointestinal disorders of the subject invention.

EXAMPLE 7

A patient who is infected with *H. pylori* and has gastritis receives four tablets of Example 6 daily for 21 days duration. The tablets are taken ½-2 hours before each meal and at bedtime. After completion of the course of therapy, the patient is free of infection by the bacterium and the associated disease.

EXAMPLE 8

A patient who is infected with *H. pylori* and has dyspepsia receives 525 mg of bismuth subsalicylate 4 times daily for 28 days. In addition, the patient also receives a capsule of Example 5 twice daily for the 28 days. After completion of this course of therapy, the patient is free of infection by the bacterium and the associated symptoms.

EXAMPLE 9

A patient who is infected with *H. pylori* and has peptic ulcer disease completes a course of therapy of 500 mg of amoxicillin 4 times daily for 14 days. The ulcer heals and infection is suppressed, but not truly eradicated. After the amoxicillin course of therapy is completed, a tablet of Example 6 is given to the patient 4 times daily for 52 weeks; the bacterial infection and associated disease symptoms remain suppressed while taking this therapy. The ulcer does not recur.

EXAMPLE 10

An individual at risk for acquiring infection by *H. pylori* is given a capsule of Example 5 one time daily for 52 weeks. The patient remains free of *H. pylori* infection during this period.

EXAMPLE 11

A patient who is infected with *H. pylori* and has peptic ulcer disease completes a course of therapy of 480 mg of bismuth subcitrate 4 times daily and 150 mg of ranitidine 2 times daily for 14 days then continuing with the same amount of ranitidine alone for another 14 days. The ulcer heals and infection is suppressed, but not truly eradicated. After this course of therapy, a capsule of Example 5 is given to the patient once daily for 52 weeks; the bacterial infection and associated disease symptoms remain suppressed while taking this therapy. The ulcer does not recur.

While particular embodiments of the subject invention have been described, it will be obvious to those skilled in the art that various changes and modifications of the subject invention can be made without departing from the spirit and scope of the invention. It is intended to cover, in the appended claims all such modifications that are within the scope of this invention.

What is claimed is:

1. A method of preventing gastroduodenal infections caused by *H. pylori* comprising orally administering to a person at risk of being infected with *H. pylori*, a safe and effective amount of a sulfated glyceroglucolipid having the structure:

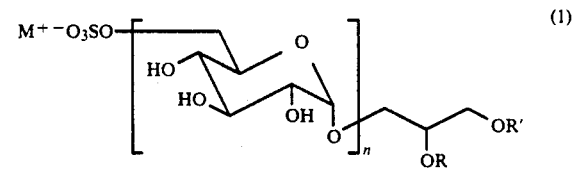

wherein n is an integer of from 1 to about 5, R is hydrogen or $C_1$-$C_{24}$ acyl or alkyl, R' is hydrogen or $C_1$-$C_{24}$ acyl or alkyl, and $M^+$ is a cationic moiety.

2. The method of claim 1 wherein R' is $C_3$-$C_{24}$ acyl or alkyl.

3. The method of claim 2 wherein n is an integer of 2 or 3.

4. The method of claim 3 wherein R is hydrogen.

5. The method of claim 1 wherein R is $C_{10}$-$C_{20}$ acyl or alkyl and R, is $C_{10}$-$C_{20}$ acyl or alkyl.

6. The method of claim 3 wherein R is $C_{10}$-$C_{20}$ acyl or alkyl and R' is $C_{10}$-$C_{20}$ acyl or alkyl.

7. The method of any of claims 1, 5 or 6 wherein the chirality of the carbon to which the —OR is bonded is in the L-form.

8. The method of any of claims 1, 5 or 6 wherein the sulfated glyceroglucolipid is administered in combination with an antimicrobial agent.

9. The method of any of claims 1, 5 or 6 wherein the sulfated glyceroglucolipid is administered in conjunction with a histamine $H_2$ receptor antagonist.

10. The method of any of claims 1, 3 or 5 wherein the sulfated glyceroglucolipid is administered at a quantity of from about 2 mg/kg to about 30 mg/kg, from 2 to 4 times daily.

11. A pharmaceutical composition comprising:
(a) a safe and effective amount of a sulfated glyceroglucolipid having the structure:

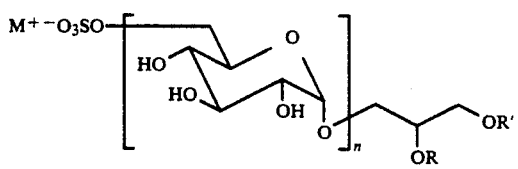

wherein n is an integer of from 1 to about 5, R is hydrogen or $C_1$-$C_{24}$ acyl or alkyl, R' is hydrogen or $C_1$-$C_{24}$ acyl or alkyl, and $M^+$ is a cationic moiety; and
(b) a pharmaceutically-acceptable carrier.

12. The composition of claim 11 wherein R' is $C_3$-$C_{24}$ acyl or alkyl.

13. The composition of claim 12 wherein n is an integer of 2 or 3.

14. The composition of claim 13 wherein R is hydrogen.

15. The composition of claim 11 wherein R is $C_{10}$-$C_{20}$ acyl or alkyl and R' is $C_{10}$-$C_{20}$ a acyl or alkyl.

16. The composition of claim 13 wherein R is $C_{10}$-$C_{20}$ acyl or alkyl and R' is $C_{10}$-$C_{20}$ acyl or alkyl.

17. The composition of any of claims 11, 15 or 16 wherein the chirality of the carbon to which the —OR is bonded is in the L-form.

18. The composition of any of claims 11, 15 or 16 wherein the composition is in dosage unit form, the dosage unit comprising from about 1 mg to about 2 g of the sulfated glyceroglucolipid.

19. The composition of any of claims 11, 13 or 15 wherein the composition is in dosage unit form, the dosage unit comprising from about 100 mg to about 1 g of the sulfated glycerylglucolipid.

* * * * *

UNITED STATES PATENT AND TRADEMARK OFFICE
CERTIFICATE OF CORRECTION

PATENT NO. : 5,116,821
DATED : May 26, 1992
INVENTOR(S) : J. L. Randall and R. D. Leunk It is certified that error appears in the above-indentified patent and that said Letters Patent is hereby corrected as shown below:

Column 1, line 56, "hexadecanpyl" should be --hexadecanoyl--.

Column 1, line 65, "hexadecanpyl" should be --hexadecanoyl--.

Column 2, line 42, "R," should be --R'--.

Column 3, line 14, "thiazpyl" should be --thiazoyl--.

Column 3, line 52, "straightchained R' is" should be --straight-chained. R' is--.

Column 4, line 15, "inilial" should be --initial--.

Column 4, line 28, "37 C" should be 37°C.

Column 8, line 2, "$C_{18}$ a reverse" should be --$C_{18}$ reverse- --.

Column 8, line 26, "Phenyl ]-Thio-β-D-glucopyranoside" should be --Phenyl 1-Thio-
β-D-glucopyranoside--.

"Column 8, line 37, "Phenyl 6-O-(tert-Butyldiohenylsilyl)-1-thio-β-D-glucopyranoside" should be --Phenyl 6-O-(tert-Butyldiphenylsilyl)-1-thio-β-D-glucopyranoside--.

Column 8, line 56, "glucooyranoside" should be --glucopyranoside--.

UNITED STATES PATENT AND TRADEMARK OFFICE
CERTIFICATE OF CORRECTION

PATENT NO. : 5,116,821
DATED : May 26, 1992
INVENTOR(S) : J. L. Randall and R. D. Leunk It is certified that error appears in the above-indentified patent and that said Letters Patent is hereby corrected as shown below:

Column 9, line 9-10, "the EtOAc 1D vacuo. The syrup obtained is subjected" should be --the EtOAc in vacuo, the syrup obtained is subjected--.

Column 9, line 15, "6-O-(tert-Butyldiohenylsilvl)" should be --6-O-(tert-Butyldiphenylsilyl)--.

Column 10, line 14, "cdoled" should be --cooled--.

Column 10, line 22, "that the reaction is complete The reaction is cooled" should be --that the reaction is complete. The reaction is cooled--.

Column 10, line 49, "L-1-O-hexadecyl-snglycerol" should be --L-1-O-hexadecyl-sn-glycerol--.

Column 10, line 50, "hexadecvl" should be --hexadecyl--.

Column 11, line 1, "Butyldiohenylsilyl" should be --Butyldiphenylsilyl--.

Column 11, line 2, "To a solution of $CH_2Cl_2$ (24 g) in $CH_2Cl_2$ (215 mL)" should be --To a solution of 11 (24 g) in $CH_2Cl_2$ (215 mL)--.

Column 11, line 15, "palmitpyl" should be --palmitoyl--.

Column 11, line 29-30, "palmitpyl-snglycerol" should be --palmitoyl-sn-glycerol--.

Column 11, line 33, "hexadecvl" should be --hexadecyl--.

UNITED STATES PATENT AND TRADEMARK OFFICE
CERTIFICATE OF CORRECTION

PATENT NO. : 5,116,821
DATED : May 26, 1992
INVENTOR(S) : J. L. Randall and R. D. Leunk It is certified that error appears in the above-indentified patent and that said Letters Patent is hereby corrected as shown below:

Column 11, line 40, "palmitpyl" should be --palmitoyl--.

Column 11, line 57, "palmitpyl" should be --palmitoyl--.

Column 11, line 60, "β" should be --α--.

Column 11, line 61, "palmitpyl" should be --palmitoyl--.

Column 12, line 7, "β" should be --α--.

Column 12, line 22, "NazSO$_4$" should be Na$_2$SO$_4$--.

Column 12, line 25, "palmitpyl" should be --palmitoyl--.

Column 12, line 28, "β" should be --α--.

Column 12, line 47, "β" should be --α--.

Column 13, line 55 and Column 13, line 56, "benzvl" should be --benzyl--.

Column 14, line 14, "β" should be --α--.

Column 14, line 17, "β" should be --α--.

Column 14, line 18, "a" should be --α--.

UNITED STATES PATENT AND TRADEMARK OFFICE
CERTIFICATE OF CORRECTION

PATENT NO. : 5,116,821
DATED : May 26, 1992
INVENTOR(S) : J. L. Randall and R. D. Leunk It is certified that error appears in the above-indentified patent and that said Letters Patent is hereby corrected as shown below:

Column 14, line 42, delete "L".

Column 14, line 56, "β" should be --α--.

Column 14, line 60, "β" should be --α--.

Column 14, line 61, "(1-6)" should be --(1-3')--.

Column 14, line 64, "D. 2 g" should be --0.2 g--.

Column 16, lines 5, and 52, after "21" delete the "," and insert a --.--.

Column 20, line 21, "1to about 5" should be --1 to about 5--.

Column 20, line 24, "$C_3-C_{24}$ acyl" should be --$C_3-C_{24}$ acyl--.

Column 20, line 30, "R" should be --R'--.

Signed and Sealed this

Thirtieth Day of August, 1994

Attest:

BRUCE LEHMAN

*Attesting Officer*      *Commissioner of Patents and Trademarks*